United States Patent

Andrus et al.

Patent Number: 5,250,360
Date of Patent: Oct. 5, 1993

[54] COATED METAL ARTICLE

[75] Inventors: Ronald L. Andrus, Elmira; John F. MacDowell, Penn Yan, both of N.Y.

[73] Assignee: Corning Incorporated, Corning, N.Y.

[21] Appl. No.: 121,076

[22] Filed: Nov. 16, 1987

[51] Int. Cl.$^5$ ............................................. B32B 9/00
[52] U.S. Cl. .................................. 428/471; 428/633; 428/450; 428/469
[58] Field of Search ............... 428/633, 450, 469, 471

[56] References Cited

U.S. PATENT DOCUMENTS

| | | | |
|---|---|---|---|
| 2,920,971 | 1/1960 | Stookey | 501/2 |
| 3,397,076 | 8/1968 | Little et al. | 428/450 |
| 3,467,534 | 9/1969 | MacDowell | 501/5 |
| 3,531,303 | 9/1970 | Bahat | 501/8 |
| 3,578,470 | 5/1971 | Bahat | 501/8 |
| 3,837,978 | 9/1974 | Busdiecker | 501/8 |
| 4,256,796 | 3/1981 | Hang et al. | 428/210 |
| 4,358,541 | 11/1982 | Andaus et al. | 501/5 |
| 4,385,127 | 5/1983 | Chyung | 501/5 |
| 4,485,151 | 11/1984 | Stecura | 428/633 |
| 4,535,033 | 8/1985 | Stecura | 428/633 |
| 4,676,994 | 6/1987 | Demaray | 427/42 |
| 4,689,270 | 8/1987 | Deckelmann et al. | 428/471 |

*Primary Examiner*—Donald P. Walsh
*Assistant Examiner*—Ngoclan T. Mai
*Attorney, Agent, or Firm*—Clinton S. Janes, Jr.

[57] ABSTRACT

There is disclosed a coated article composed of a metal alloy substrate, the metal alloy having a nickel, chromium, cobalt or iron base, and a coating that serves as an oxygen barrier to insulate the metal surface from oxygen attack at temperatures which may range up to 1200° C. The coating comprises a glass-ceramic selected from barium silicate and strontium silicate systems characterized by additives that enable forming a continuous well flowed glass coating prior to setting of the coating by crystallization. These additives include the refractory oxides $Al_2O_3$, $ZrO_2$ and $Y_2O_3$, the transition metal oxides MnO, CoO, NiO and FeO, and MgO.

22 Claims, 1 Drawing Sheet

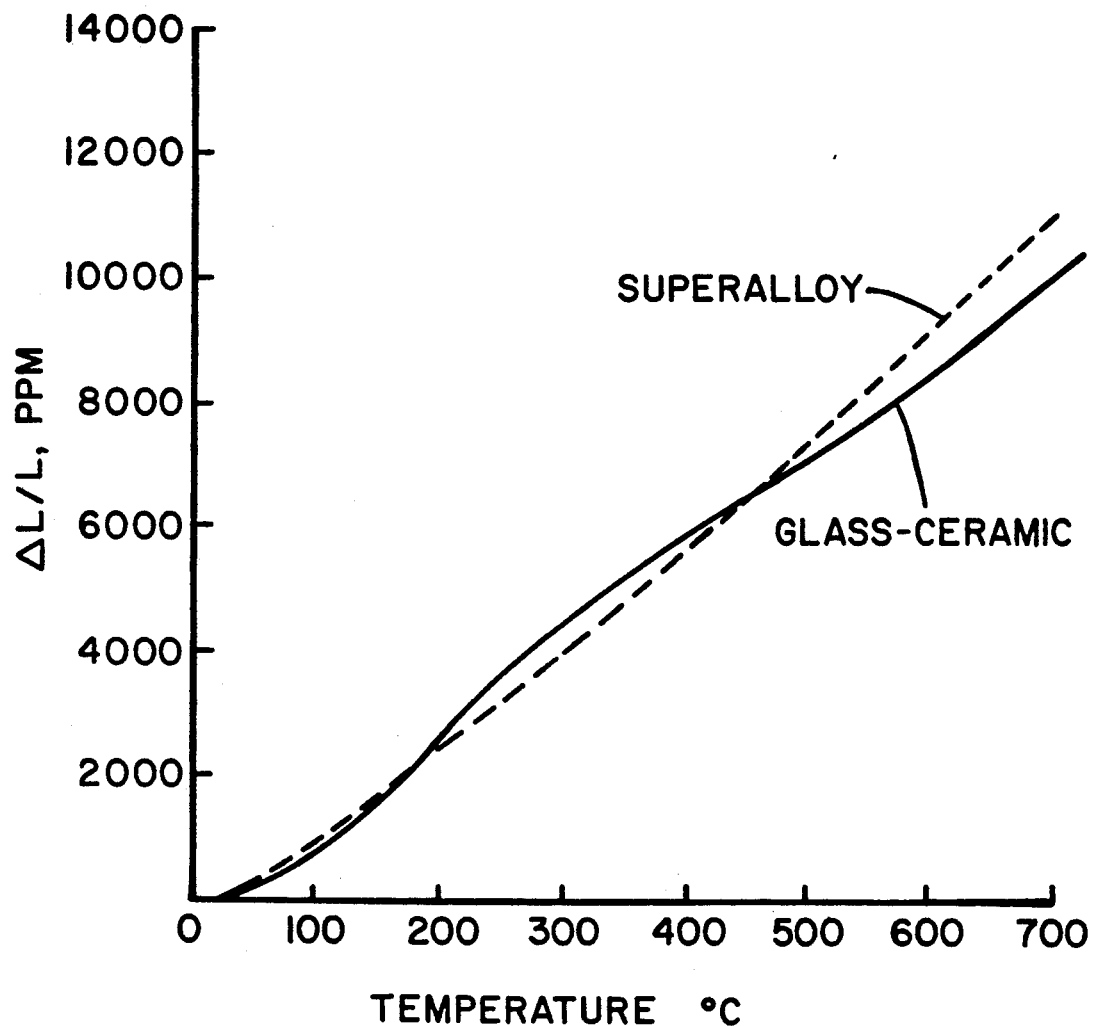

COATED METAL ARTICLE

This invention relates to a coated article composed of a metal alloy substrate having a coating comprising a glass-ceramic selected from the barium silicate or strontium silicate system. The coating over the surface of the metal substrate serves as an oxygen barrier to prevent oxygen attack of the metal at elevated temperatures and as a thermal barrier to prevent rapid heatup of the metal.

There is a well recognized need, in turbine engines and heat exchangers, for example, for materials capable of withstanding operating temperatures in excess of 1000° C. While a variety of high temperature materials are known, it is common practice to use alloys known as superalloys in the more severe applications. Characteristically, these alloys are rich in nickel, cobalt, chromium, or iron, with nickel or cobalt being the principal metal bases. The superalloys have been distinguished from other high temperature materials on the basis of being sufficiently resistant to oxidation to permit operation in an oxidizing atmosphere without a barrier coating. Nevertheless, under severe conditions, such as encountered by turbine blades in aircraft engines, even the superalloys tend to deteriorate unless protected by a barrier coating.

A common method of protecting materials from oxidation at elevated temperatures is to apply a continuous monolithic glass coating. This completely encapsulates and isolates the material from the surrounding (oxygen-containing) atmosphere. However, viscous flow of the glass coating may occur when large surface stresses develop during high temperature use. In that case, a glass barrier coating tends to develop thin spots and fail catastrophically.

The high temperature viscosity of the glass coatings may be increased by mixing crystalline materials with the glass frits before application of the coating. However, these glass-crystalline mixtures sinter rather non-uniformly, the crystal size and homogeneity being very difficult to control. Certain portions of the substrate, therefore, tend to be entirely free from crystals, whereas other portions have too many (or too large) crystals to sinter well. A void-free coating with this heterogeneous glass-crystal mixture is thus difficult to obtain.

Accordingly, to protect superalloy parts, insulating layers of stabilized $ZrO_2$ are now commercially applied via a plasma-spraying technique. U.S. Pat. No. 4,485,151 and No. 4,535,033 (Stecura) describe such a procedure using an alloy as a bond for the stabilized zirconia. U.S. Pat. No. 4,676,994 (Demeray) describes a procedure wherein an oxidized alloy of aluminum is employed as an intermediate coating.

These procedures involve several steps that are tedious and difficult to control in commercial production. Further, thermal gradients tend to develop during plasmaspraying and introduce defects in the finished coating. Also, the coatings tend to be porous. This permits access of gases, in particular $O_2$, $SO_2$, and water vapor, all of which can contribute to coating failure. Nevertheless, such procedures are used extensively to protect selected jet engine parts from corrosion oxidation failure between normal periodic overhauls.

PURPOSE OF THE INVENTION

A basic purpose is to provide a reliable and reproducible oxygen barrier coating for superalloy bodies that are required to operate at temperatures above 1000° C.

Another purpose is to provide such a coating that is more effective, and easier to apply, than previously known coatings.

A further purpose is to provide an oxygen barrier coating that is non-porous, continuous and free from defects, such as pinholes and cracks.

A still further purpose is to provide an oxygen barrier coating that adheres tightly and resists spalling during thermal cycling.

Another purpose is to provide an oxygen barrier coating material that exhibits the excellent flow characteristics of a glass coating as it is fired in one temperature range, and becomes resistant to flow (due to crystallization) as it is heated in a higher temperature range.

A further purpose is to provide a superalloy metal body having an oxygen barrier coating that adapts the body to operating temperatures up to 1200° C.

A still further purpose is to provide a useful degree of thermal insulation to the metal surface.

SUMMARY OF THE INVENTION

The invention resides in a coated article adapted to operate at temperatures above 1000° C. in an oxygen-containing environment and comprising a metal alloy substrate, the metal alloy being selected from the group consisting of nickel-base, cobalt-base, chromium-base and iron-base alloys, and a coating forming an oxygen barrier over the metal surface, the coating comprising a glass-ceramic having a composition, on an oxide basis in weight percent, selected from a barium silicate and a strontium silicate system, the barium silicate system containing 20-65% BaO and 25-65% $SiO_2$, the strontium silicate system containing 20-60% SrO and 30-70% $SiO_2$, each system additionally consisting essentially of at least one oxide selected from the group consisting of up to 15% $Al_2O_3$, up to 15% $ZrO_2$, up to 15% $Y_2O_3$, up to 25% MnO, up to 25% NiO, up to 30% MgO, up to 30% CoO and up to 40% iron oxide, and containing not over 5% $B_2O_3+R_2O$, the total of all such additions not exceeding 50% in the barium silicate system and 40% in the strontium silicate system.

Preferably the selected oxide is $Al_2O_3$ or $ZrO_2$ and the composition is free of $R_2O$ and $B_2O_3$.

In a preferred range in the barium silicate system, the compositions consist essentially of $SiO_2$ BaO in mole ratios of 2:1 to 5:1 (approximately 40-65% $SiO_2$ and 30-55% BaO, both in percent by weight) and 1-10% by weight $Al_2O_3$ Likewise, preferred ranges in the strontium silicate system consist essentially of $SiO_2$:SrO in mole ratios of 1.5:1 to 4:1 (approximately 45-65% $SiO_2$ and 30-55% SrO by weight) and 5-10 mole percent $ZrO_2$ or $Al_2O_3$.

PRIOR LITERATURE

Attention is directed to the following U.S. Pat.:

No. 3,397,076 (Little et al.) describes fused crystallizable ground and cover coats for high temperature alloys in which the major elements are cobalt, nickel, chromium, iron or mixtures. The ground coat is lithium-free and contains 35-65% $SiO_2$ and 12-45% BaO. Examples also contain substantial amounts of $R_2O$, $B_2O_3$ and/or $TiO_2$.

No. 3,467,534 (MacDowell) discloses glass-ceramic articles consisting essentially of 20–70% BaO and 30–80% $SiO_2$ and having a barium silicate principal crystal phase. A preferred example is described as considered for coating metals.

No. 3,531,303 (Bahat) discloses glass-ceramic articles in the alkaline earth aluminosilicate field wherein a hexagonal alkaline earth feldspar or a triclinic form is the principal crystal phase. The materials are highly refractory with service temperatures up to 1700° C. and consist essentially of 12–53% $SiO_2$, 17–55% RO where RO is 17–50% SrO and 20–50% BaO, 10–58% $Al_2O_3$ and a nucleating agent.

No. 3,578,470 (Bahat) discloses glass-ceramic materials in the $BaO-Al_2O_3-SiO_2$ composition field nucleated with $Ta_2O_5$ and/or $Nb_2O_5$ that are especially suited to sealing with tungsten or molybdenum and their alloys.

No. 3,837,978 (Busdiecker) discloses barium aluminosilicate glass-ceramics nucleated by tin oxide, having a hexacelsian primary crystal phase, and having a coefficient of thermal expansion in the range of $50-170 \times 10^{-7}/°$ C.

GENERAL DESCRIPTION

Our invention provides a very effective oxygen barrier over the surface of a metal alloy substrate. The barrier is a coating comprising a barium silicate or strontium silicate glass-ceramic material. The coating is continuous, free from defects such as pinholes, cracks, or thin spots and resists spalling during temperature cycling.

The invention is based, to a considerable degree, on our discovery that certain additives have an unusual effect on the crystallization properties of thermally crystallizable, barium silicate and strontium silicate glasses. In particular, these additives permit the glass to soften and flow into a continuous, glassy coating before sufficient crystallization occurs to impede flow. Absent at least one of these additives, the glass tends to stiffen by crystallization before complete coverage occurs. The result is a porous, cracked coating. This discovery is the key to producing an effective oxygen barrier on a superalloy surface.

Another significant requirement in producing an effective oxygen barrier coating is a close thermal expansion match between the coating and the metal body. The thermal expansion coefficients of the superalloys are usually between 130 and $160 \times 10^{-7}/°$ C. This precludes many refractory glasses and ceramics from consideration. As mentioned earlier, it has also led to using a bonding layer.

The principal crystal phases in the glass-ceramics of the present invention are usually barium or strontium silicates. However, we have observed that there usually is a cristobalite phase present, and this may be the principal phase. Further, we have observed that there is a strong tendency for cristobalite crystals to be concentrated in a zone adjacent the interface with the superalloy surface.

It is our belief that the coefficient of thermal expansion match depends on this concentration of cristobalite crystals, rather than solely upon the expansion coefficient of the glass-ceramic. It is our further belief that metal ions, migrating from the alloy into the glass as it is being heated, are responsible for nucleating the cristobalite crystals near the interface.

Superalloys are well known in the metallurgical art. In general, they are highly refractory, withstanding operating temperatures in excess of 1000° C. They find application in such equipment as turbine engines, air preheaters and heat exchangers.

Superalloys do not have fixed composition limits. Rather, they are generally classed according to the base metal. The base metals include nickel, iron, chromium and cobalt, with nickel being the most commonly used base metal. Among the known series of nickel-base superalloys are the Nimonic, Inconel, Mastelloy, Hastelloy, Waspaloy and Rene series. The cobalt superalloys include the Mar-M and AR- series.

The superalloys are said to be sufficiently resistant to oxidation to permit operation in an oxidizing atmosphere without a surface coating. This resistance is conferred in nickel-base alloys by chromium and/or aluminum additions. Nevertheless, under severe operating conditions, such as encountered by turbine blades for aircraft engines, even the superalloys tend to deteriorate rapidly unless protected by an oxygen barrier coating.

The search for a coating capable of withstanding temperatures higher than available glasses naturally led to the field of glass-ceramics. Glass-ceramic materials, and their production, were first described in U.S. Pat. No. 2,920,971 (Stookey). Briefly, in producing a glass-ceramic coating material, a thermally crystallizable glass is melted and quickly cooled to avoid crystallization. Subsequently, the quenched glass is powdered and applied as a coating. The powdered glass coating is then heated to precipitate a fine dispersion of nuclei. These nuclei act as centers for further crystallization of a primary crystal phase as the glass is heated to a higher temperature.

In theory, a glass-ceramic coating should retain the excellent oxygen barrier characteristics of the original glassy coating. Further, the formation of a crystalline network should stiffen the glass and render it resistant to flow once a coating is formed. Thus, the glass-ceramic coating should provide a reliable barrier to oxygen up to the temperature at which the crystal phase starts to dissolve. However, previous studies have indicated that crystallization tends to occur too early. This precludes the degree of glass flow required to produce a continuous, glassy coating.

Ceramics having a high expansion coefficient commonly contain rather large quantities of alkali oxides ($Li_2O$, $Na_2O$, or $K_2O$). These alkali ions are extremely mobile in most ceramic structures at high temperatures, and readily exchange for other ions. Therefore, they must be eliminated as major constituents in coatings that must continually operate at high temperatures. This leaves but few candidates for refractory coatings.

Mixed barium magnesium and calcium magnesium silicate coatings, fluxed with $B_2O_3$, are described in U.S. Pat. Nos. 4,256,796, 4,358,541 and 4,385,127. The limiting factor in the high temperature resistance of these coatings is the use of $B_2O_3$. A high $B_2O_3$ residual glass (or even a borate crystal) tends to allow the microstructure to move and flow at temperatures much below the solidus of the primary refractory silicate phases. Accordingly, our present coatings are formulated with little or no boric oxide.

We have found that the addition of small amounts of the refractory, glass-forming oxides $Al_2O_3$, $ZrO_2$ and $Y_2O_3$ alters the crystallization behavior in crystallizable barium silicate and strontium silicate glasses. In particular, these additives delay crystallization to such an extent that the glass can soften and flow to form a continuous coating before the glass becomes dense and stiff due to crystallization.

While these oxides are very effective in delaying crystallization, their use must be limited. The amount should not exceed about 15%, and preferably is not over about 10% by weight. Otherwise, undesirable crystal phases, such as aluminosilicates which may have low expansion coefficients or other detrimental properties, tend to form.

The most effective of the refractory oxide additives is $Al_2O_3$. Thus, the best barium silicate coatings employ the $BaO-SiO_2$ binary system with an $Al_2O_3$ addition of one to 10% by weight and a $SiO_2$ BaO mole ratio between about 2:1 and 5:1.

We have also found that certain transition metal oxides, as well as MgO, are effective in barium silicate glasses to provide a continuous, well-flowed glass coating prior to crystallization. The transition metal oxides include MnO, NiO, CoO and FeO and/or $Fe_2O_3$.

Manganese oxide additions were found particularly effective in producing coatings with excellent adherence, good flow before crystallization and spall resistance. However, with substantial amounts of MnO present, the crystal phases tended to dissolve above about 1050° C., thus limiting the refractoriness of coatings containing this oxide. The crystal phases formed below 1050° C. were $Ba_2MnSi_2O_7$ and cristobalite.

Barium silicate coatings containing FeO, CoO or NiO were not as smooth and adherent as the manganese-containing coatings. However, they were at least 100° C. more refractory. In these coatings, alpha-$BaSi_2O_5$ (sanbornite) was the principal crystalline phase with small amounts of alpha-cristobalite. Small additions, generally less than 5 mole percent, of glass-forming oxides, such as $ZrO_2$, $Al_2O_3$, $CeO_2$, $TiO_2$, $Nb_2O_5$ and $B_2O_3$, improved the flow and appearance of the coatings.

In addition to BaO or SrO, $SiO_2$ and one or more of the refractory and transition metal oxide modifiers, our barium and strontium silicate coating compositions may optionally include up to about 25% by weight of other oxides. This includes 0–25% ZnO, 0–10% $TiO_2$, 0–20% CaO, 0–20% SrO, 0–20% $NbO_5$, and 0–10% F.

The alkali metal oxides $Na_2O$, $K_2O$ and $Li_2O$ ($R_2O$), as well as $B_2O_3$, are preferably excluded. These flux oxides tend to lower the thermal effectiveness of the coating and increase the coefficient of expansion. However, in some cases, they may be tolerated in amounts up to 5 wt. %.

In working with the barium silicate system coatings, it was observed that good adherence was obtained when the coating was fired in a predominantly helium atmosphere. This was true even though as much as 5% oxygen might be present. However, adherence was not nearly as good when the coating was fired in air (~21% oxygen).

This led to a study of the strontium silicate system. Surprisingly, strontium silicate coatings usually provide equally excellent adherant coatings whether fired in air or in a helium atmosphere. This renders the strontium silicate-based coatings more practical for many applications.

As in the case of the barium silicate system, small additions of $Al_2O_3$, $ZrO_2$, or $Y_2O_3$, up to about 15% by weight, are helpful in promoting adequate glass flow prior to substantial crystallization and stiffening of the coating. A preferred strontium silicate system contains 5 to 10 mole percent $Al_2O_3$ or $ZrO_2$ and a $SiO_2$:SrO mole ratio in the range 1.5:1 to 4:1.

The strontium silicate base coatings are well crystallized, smooth and adherent. They may contain $SrSiO_3$ as a major crystal phase, with a small amount of cristobalite. However, as in the barium system, the cristobalite may be the primary phase. The cristobalite appears to concentrate at the interface of the coating and metal. As in the barium silicate system, this produces a strong bond that resists spalling when cycled, and apparently provides a good expansion match.

Manganese, nickel, zinc and magnesium oxides, in combination with approximately equimolar amounts of SrO, are effective to produce good glass flow and hence useful coatings. However, optimum results usually are obtained with the presence of at least some $Al_2O_3$ and/or $ZrO_2$. In the presence of the transition metal oxides and MgO, crystal phases such as $Sr_2MgSi_2O_7$, $Sr_2ZnSi_2O_7$ and silicates of nickel and manganese may be observed as the primary silicate phase.

The strontium silicate compositions, like the barium silicates, may contain additional oxides, beyond the modifier oxides, in amounts up to 25%. These include 0–25% ZnO, 0–20% CaO, 0–10% F, 0–10% $TiO_2$, 0–20% $Nb_2O_5$ and 0–20% BaO. Again $R_2O$ and $B_2O_3$ may be tolerated in minor amounts, but are preferably excluded.

In practicing the invention, the surface of a preformed superalloy body may be coated with powdered glass in any conventional manner. The method we prefer is electrostatic spraying, wherein electrostatically-charged, dry glass powder is very uniformly sprayed onto the superalloy body, which is supported on an oppositely charged wire mesh screen. Alternatively, the powdered glass may be mixed with a suitable medium, e.g., water or an organic vehicle, applied uniformly over the glass surface and dried.

The glass powder-coated metal body is then heated to a temperature below 1000° C. This softens the glass particles and produces a dense, smooth, well-formed continuous glass coating that is essentially free from crystallization. The glass-coated body is then heated to a somewhat higher temperature. This effects development of a crystal phase which forms a dense, strong, refractory, crystalline coating. A key feature of this procedure is the ability to control the timing of crystallization, and thus the reproducibility of the coating process.

The coating has been described in terms of applying a pulverized glass over the surface of a superalloy substrate. However, it will be appreciated that fillers, and additives for other purposes, may be incorporated with the powdered glass to the extent that such additives do not prevent the pulverized glass particles from flowing into a continuous glassy coating.

DESCRIPTION OF THE DRAWING

The single FIGURE in the accompanying drawing is a graphical illustration of two thermal expansion curves. Thermal expansion, $\Delta L/L$, in parts per million (ppm), is plotted along the vertical axis; and temperature, in ° C. is plotted along the horizontal axis. The solid line curve represents values for the glass-ceramic coating of Example 11 in TABLE I, infra; the broken line curve represents values for a typical superalloy Inconel 718. A good match is seen between the thermal expansion behavior of the superalloy and that of a typical barium silicate glass-ceramic coating.

SPECIFIC DESCRIPTION

The invention is further described with respect to several specific examples of glass-ceramic materials that may be applied as coatings on superalloy bodies in accordance with the invention. These materials are capable of yielding smooth, adherent, non-porous coatings that have little or no tendency to spall during temperature cycling. This indicates a close expansion match in the vicinity of the interface.

TABLE I lists compositions in the barium silicate system; TABLE II lists compositions in the strontium silicate system. In each composition, the constituents are given on the oxide basis. The compositions are shown in both percent by weight (Wt. %) and mole ratio (M.R.).

TABLE I

| | BARIUM SILICATE COMPOSITIONS | | | | | |
|---|---|---|---|---|---|---|
| Oxides | Wt. % | M.R | Wt. % | M.R. | Wt. % | M.R. |
| | 1 | | 2 | | 3 | |
| $SiO_2$ | 61.9 | 4.5 | 55.8 | 3.5 | 47.5 | 2.5 |
| BaO | 35.2 | 1 | 40.8 | 1 | 48.5 | 1 |
| $Al_2O_3$ | 2.9 | 0.125 | 3.4 | 0.125 | 4.0 | 0.125 |
| | 4 | | 5 | | 6 | |
| $SiO_2$ | 45.6 | 2.5 | 57.3 | 4 | 44.9 | 2.5 |
| BaO | 46.6 | 1 | 36.6 | 1 | 45.9 | 1 |
| $Al_2O_3$ | 7.8 | 0.25 | 6.1 | 0.25 | | |
| $ZrO_2$ | | | | | 9.2 | 0.25 |
| | 7 | | 8 | | 9 | |
| $SiO_2$ | 53.3 | 4 | 51.6 | 4 | 31.1 | 2 |
| BaO | 34.1 | 1 | 33.0 | 1 | 59.6 | 1.5 |
| $Y_2O_3$ | 12.6 | 0.25 | | | | |
| FeO | | | 15.4 | 1 | 9.3 | 0.5 |
| | 10 | | 11 | | 12 | |
| $SiO_2$ | 39.4 | 2 | 38.6 | 2 | 28.3 | 1.5 |
| BaO | 25.2 | 0.5 | 49.3 | 1 | 48.2 | 1 |
| CoO | | | 12.1 | 0.5 | 23.5 | 1 |
| FeO | 35.4 | 1.5 | | | | |
| | 13 | | 14 | | 15 | |
| $SiO_2$ | 46.7 | 2 | 34.9 | 2 | 32.0 | 2 |
| BaO | 29.8 | 0.5 | 44.5 | 1 | 40.9 | 1 |
| MgO | 23.5 | 1.5 | | | | |
| MnO | | | 20.6 | 1 | 18.9 | 1 |
| F | | | 3.0 | 0.5 | | |
| $ZrO_2$ | | | | | 8.2 | 0.25 |
| | 16 | | 17 | | 18 | |
| $SiO_2$ | 33.6 | 2 | 33.9 | 2 | 33.2 | 2 |
| BaO | 43.0 | 1 | 43.2 | 1 | 42.4 | 1 |
| $ZrO_2$ | 3.5 | 0.1 | | | | |
| MnO | 19.9 | 1 | 20.0 | 1 | 19.6 | 1 |
| $Al_2O_3$ | | | 2.9 | 0.1 | | |
| $B_2O_3$ | | | | | 4.8 | 0.2 |
| | 19 | | 20 | | 21 | |
| $SiO_2$ | 32.9 | 2 | 31.0 | 2 | 29.2 | 2 |
| BaO | 42.1 | 1 | 39.6 | 1 | 37.3 | 1 |
| MnO | 19.5 | 1 | 18.3 | 1 | 17.3 | 1 |
| $Nb_2O_5$ | | | | | 16.2 | 0.1 |
| $TiO_2$ | 5.5 | 0.1 | | | | |
| $CeO_2$ | | | 11.1 | 0.1 | | |
| | 22 | | 23 | | 24 | |
| $SiO_2$ | 32.2 | 2 | 31.7 | 2 | 37.1 | 2 |
| BaO | 41.0 | 1 | 40.5 | 1 | 47.3 | 1 |
| $Al_2O_3$ | 6.8 | 0.25 | | | 3.2 | 0.1 |
| NiO | 20.0 | 1 | 19.7 | 1 | | |
| $ZrO_2$ | | | 8.1 | 0.25 | | |
| MgO | | | | | 12.4 | 1 |
| | 25 | | | | | |
| $SiO_2$ | 35.3 | 2 | | | | |
| BaO | 45.2 | 1 | | | | |
| $Al_2O_3$ | 3.0 | 0.1 | | | | |

TABLE I-continued

| | BARIUM SILICATE COMPOSITIONS | | | | | |
|---|---|---|---|---|---|---|
| Oxides | Wt. % | M.R | Wt. % | M.R. | Wt. % | M.R. |
| CaO | 16.5 | 1 | | | | |

TABLE II

| | STRONTIUM SILICATE COMPOSITIONS | | | | | |
|---|---|---|---|---|---|---|
| Oxides | Wt. % | M.R | Wt. % | M.R. | Wt. % | M.R. |
| | 26 | | 27 | | 28 | |
| $SiO_2$ | 48.2 | 2 | 58.3 | 3 | 65.0 | 4 |
| SrO | 41.6 | 1 | 33.5 | 1 | 28.1 | 1 |
| $Al_2O_3$ | 10.2 | 0.25 | 8.2 | 0.25 | 6.9 | 0.25 |
| | 29 | | 30 | | 31 | |
| $SiO_2$ | 40.1 | 1.5 | 47.2 | 2 | 52.8 | 2.5 |
| SrO | 46.2 | 1 | 40.7 | 1 | 36.4 | 1 |
| $ZrO_2$ | 13.7 | 0.25 | 12.1 | 0.25 | 10.8 | 0.25 |
| | 32 | | 33 | | 34 | |
| $SiO_2$ | 40.7 | 2 | 40.6 | 2 | 38.3 | 2 |
| SrO | 35.2 | 1 | 35.2 | 1 | 33.1 | 1 |
| $ZrO_2$ | | | 10.5 | 0.25 | 5.9 | 0.15 |
| MnO | 24.1 | 1 | | | 22.7 | 1 |
| MgO | | | 13.7 | 1 | | |
| | 35 | | 36 | | 37 | |
| $SiO_2$ | 36.9 | 2 | 35.7 | 2 | 54.2 | 4 |
| SrO | 31.9 | 1 | 30.9 | 1 | 23.3 | 1 |
| $ZrO_2$ | 9.5 | 0.25 | 9.2 | 0.25 | | |
| $Al_2O_3$ | | | | | 5.7 | 0.25 |
| MnO | 21.7 | 1 | | | | |
| ZnO | | | 24.2 | 1 | | |
| NiO | | | | | 16.8 | 1 |

Glass batches, corresponding to each of the compositions in TABLES I and II, were mixed. The batches were melted in platinum crucibles at 1600° C. for two hours. The glass melts thus obtained were poured into water to quench and granulate the glass. The granular glass was ball milled with alumina cylinders for 4 to 8 hours to provide powdered glass with an average particle size of 10 to 15 micrometers.

Powdered glasses were dry pressed in the form of cylinders ½" in diameter. These were heat treated at temperatures of 800–1200° C. for ½-1 hour to determine sintering characteristics and density (non-porosity). Additionally, 4"×¼"×¼" bars were pressed and fired for determination of thermal expansion coefficient (Exp.) expressed in terms of ×10⁻⁷/° C. X-ray diffraction traces were made on fired samples to determine crystal phases developed during firing.

TABLES III and IV list properties observed on the glass-ceramics prepared from the compositions of TABLES I and II. The example numbers of the TABLES correspond for cross reference.

Promising glasses were applied on Inconel 718 substrates and fired. The heat treatments are shown in the TABLES in terms of temperature in ° C. (Temp.), time in hours (T) and atmosphere (Atm.), either helium (He) or air. In the case of barium silicate glassceramics, a helium atmosphere, although it contained as much as 20% air, proved much more effective for obtaining good coatings. It appeared that, with an air atmosphere too much oxidation of the metal surface occurred before a continuous glass coating formed. While slight spalling and/or porosity was observed with some coatings, this was not serious. It is anticipated that fine tuning of the processing could avoid these conditions.

TABLE III

BARIUM SILICATE COATINGS ON INCONEL 718 SUPERALLOY

| Ex. | Temp. | T. | Atm. | Appearance | Exp. 25–300° C. | Crystal Phases |
|---|---|---|---|---|---|---|
| 1. | 1100° | 1 hr. | (He) | slightly porous | 197.7 | $\beta$-$BaSi_2O_5$, $\alpha$-cristobalite |
|  | 1200° | 1 hr. | (He) | glossy blue-grey |  |  |
|  | 1100° | 1 hr. | (Air) | no adherence |  |  |
| 2. | 1100° | 1 hr. | (He) | rough-textured blue-white | 152.7 | $\beta$-$BaSi_2O_5$, $\alpha$-cristobalite |
|  | 1200° | 1 hr. | (He) | glossy blue-grey, some pinholes |  |  |
|  | 1100° | 1 hr. | (Air) | no bonding |  |  |
| 3. | 1100° | 1 hr. | (He) | textured dark grey | 107.3 | $\alpha$-cristobalite, $\beta$-$BaSi_2O_5$ |
|  | 1200° | 1 hr. | (He) | edge blisters |  | $\beta$-$BaSi_2O_5$, $\alpha$-cristobalite |
|  | 1100° | 1 hr. | (Air) | no bonding |  |  |
| 4. | 1100° | 1 hr. | (He) | slight edge spall | 91.3 | $\beta$-$BaSi_2O_5$ |
|  | 1100° | 1 hr. | (Air) | 90% spalled off |  |  |
| 5. | 1100° | 1 hr. | (He) | glassy, transparent | 112.6 | $\alpha$-cristobalite |
|  | 1200° | 1 hr. | (He) | few bubbles |  |  |
|  | 1100° | 1 hr. | (Air) | pitted and spalled |  |  |
| 6. | 1100° | 1 hr. | (He) | sl. spall | 94.8 | $\beta$-$BaSi_2O_5$ |
|  | 1100° | 1 hr. | (Air) | coating spalled off |  |  |
| 7. | 1100° | 1 hr. | (He) | few pinholes |  | $\beta$-$BaSi_2O_5$, $\alpha$-cristobalite |
|  | 1200° | 1 hr. | (He) | sl. spall |  |  |
|  | 1100° | 1 hr. | (Air) | sl. textured |  |  |
| 8. | 1100° | 1 hr. | (He) | sl. edge spall | 148.0 | $\alpha$-cristobalite |
|  | 1100° | 1 hr. | (Air) | sl. edge spall |  |  |
| 9. | 1100° | 1 hr. | (He) | sl. rippled |  | $\beta$-$BaSi_2O_5$ |
|  | 1100° | 1 hr. | (Air) | sl. edge spall |  |  |
| 10. | 1100° | 1 hr. | (He) | textured |  | $\alpha$-cristobalite, $Fe_2O_3$ |
|  | 1100° | 1 hr. | (Air) | spalled end |  |  |
| 11. | 1100° | 1 hr. | (He) | rough textured |  | $\beta$-$BaSi_2O_5$ |
|  | 1100° | 1 hr. | (Air) | textured |  |  |
| 12. | 1100° | 1 hr. | (He) | glossy |  |  |
|  | 1100° | 1 hr. | (Air) | some spall |  |  |
| 13. | 1100° | 1 hr. | (He) | sl. spalling |  | $\beta$-$BaSi_2O_5$, $BaMgSi_4O_{10}$ |
| 14. | 1100° | 1 hr. | (He) | glossy black |  |  |
|  | 1100° | 1 hr. | (Air) | sl. spall |  |  |
| 15. | 1100° | 1 hr. | (He) | smooth | 105.6 | $\alpha$-cristobalite |
|  | 1200° | 1 hr. | (He) | sl. bumpy texture |  |  |
|  | 1100° | 1 hr. | (Air) | sl. spalling |  |  |
| 16. | 1100° | 1 hr. | (He) | smooth |  | $\alpha$-cristobalite |
|  | 1100° | 1 hr. | (Air) | melted & puddled |  |  |
| 17. | 1100° | 1 hr. | (He) | glossy |  | amorphous |
|  | 1100° | 1 hr. | (Air) | melted & puddled |  |  |
| 18. | 1000° | ½ hr. | (He) | smooth glossy | 92.4 |  |
|  | 1100° | 1 hr. | (Air) | puddled & melted |  |  |
| 19. | 1000° | ½ hr. | (He) | sl. rippled | 84.8 | $Ba_2MnSi_2O_7$ |
|  | 1100° | 1 hr. | (Air) | semi-gloss |  |  |
| 20. | 1000° | ½ hr. | (He) | sl. rippled | 91.4 | $Ba_2MnSi_2O_5$ |
|  | 1100° | 1 hr. | (Air) | semi-gloss |  |  |
| 21. | 1000° | ½ hr. | (He) | smooth, glossy | 79.5 | amorphous |
|  | 1100° | 1 hr. | (Air) | glossy |  |  |
| 22. | 1100° | 1 hr. | (He) | smooth | 69.1 | $\beta$-$BaSi_2O_5$ |
|  | 1200° | 1 hr. | (He) | smooth |  |  |
|  | 1100° | 1 hr. | (Air) | sl. edge spall |  |  |
| 23. | 1100° | 1 hr. | (He) | rough textured | 152.1 | $\alpha$-cristobalite |
|  | 1200° | 1 hr. | (He) | matte |  |  |
|  | 1100° | 1 hr. | (Air) | sl. porous |  |  |
| 24. | 1100° | 1 hr. | (He) | smooth, glossy | 78.1 | $BaMg_2Si_2O_7$ |
|  | 1100° | 1 hr. | (Air) | some spall |  |  |
| 25. | 1100° | 1 hr. | (He) | thick matte | 83.1 | $\beta$-$BaSi_2O_5$ |

TABLE III-continued
BARIUM SILICATE COATINGS ON INCONEL 718 SUPERALLOY

| Ex. | Temp. | T. | Atm. | Appearance | Exp. 25–300° C. | Crystal Phases |
|---|---|---|---|---|---|---|
|  | 1100° | 1 hr. | (Air) | spalling |  |  |

TABLE IV
STRONTIUM SILICATE COATINGS ON INCONEL 718 SUPERALLOY

| Ex. | Temp. | T. | Atm. | Appearance | Exp. 25–300° C. | Crystal Phases |
|---|---|---|---|---|---|---|
| 26. | 1100° | 1 hr. | (He) | smooth grey | 65.6 | SrSiO$_3$ |
|  | 1200° | 1 hr. | (He) | pinholes, spalling |  |  |
|  | 1100° | 1 hr. | (Air) | sl. spalling at edges |  |  |
| 27. | 1100° | 1 hr. | (He) | smooth | 82.8 | α-cristobalite |
|  | 1100° | 1 hr. | (Air) | glossy |  |  |
| 28. | 1100° | 1 hr. | (He) | smooth | 135.9 | α-cristobalite |
|  | 1200° | 1 hr. | (He) | smooth |  |  |
|  | 1100° | 1 hr. | (Air) | glossy |  |  |
| 29. | 1100° | 1 hr. | (He) | sl. spalling | 96.4 | SrSiO$_3$ |
|  | 1100° | 1 hr. | (Air) | no adherance |  |  |
| 30. | 1100° | 1 hr. | (He) | smooth glossy |  | SrSiO$_3$, α-cristobalite |
| 31. | 1100° | 1 hr. | (He) | sl. rippled |  | SrSiO$_3$, α-cristobalite |
|  | 1100° | 1 hr. | (Air) | semigloss |  |  |
| 32. | 1100° | 1 hr. | (He) | smooth |  |  |
|  | 1100° | 1 hr. | (Air) | sl. textured |  |  |
| 33. | 1100° | 1 hr. | (He) | semigloss |  | Sr$_2$MgSi$_2$O$_7$ |
|  | 1100° | 1 hr. | (Air) | spalled off |  |  |
| 34. | 1100° | 1 hr. | (He) | smooth |  | Mn$_7$SiO$_{12}$ |
|  | 1100° | 1 hr. | (Air) | semi-gloss |  |  |
| 35. | 1100° | 1 hr. | (He) | smooth |  | Ni$_2$SiO$_4$, αc-cristobalite |
|  | 1100° | 1 hr. | (Air) | sl. spalling |  |  |
| 36. | 1100° | 1 hr. | (He) | sl. edge spall |  | SrZnSi$_2$O$_7$, SrZnSi$_2$O$_7$ |
| 37. | 1100° | 1 hr. | (He) | rippled | 130.0 | SrSiO$_3$, Ni$_2$SiO$_4$ |
|  | 1200° | 1 hr. | (He) | smooth |  |  |
|  | 1100° | 1 hr. | (Air) | sl. textured |  |  |

TABLE V displays the results of flame cycle testing of four exemplary coatings selected from those shown in TABLES I and II. Corresponding example numbers are used for convenience in cross-reference.

Test samples were prepared by coating both sides of Inconel 718 superalloy bodies with pulverized glass as described earlier. The glass coated bodies were fired at 1100° C. for one hour in a helium atmosphere. The samples, thus prepared, were mounted on a holder and cycled 600 times. Each cycle consisted of (1) 5 minutes with a flame impinging on the samples and (2) 5 minutes cooling in air. Sample temperatures reached about 1050° C. during each cycle. Three of the four samples showed no evidence of spalling. This was an excellent result considering the severity of the thermal gradients and overall thermal shock engendered.

TABLE V

| Sample No. | Coating | Appearance |
|---|---|---|
| 11. | BaO—SiO$_2$ | Discolored, slight blistering, no spalling |
| 22. | BaO—SiO$_2$ | Discolored, but no spalling |
| 27. | SrO—SiO$_2$ | Blistering on flame exposed corner, no spalling |
| 28. | SrO—SiO$_2$ | Flame exposed corner spalled |

We claim:

1. A coated article adapted to operate at temperature above 1000° C. in an oxygen-containing environment, said article comprising a superalloy substrate, the superalloy being selected from the group consisting of nickel-based, cobalt-based, chromium-based, and iron-based alloys, and a coating forming an oxygen barrier over the superalloy surface, the coating exhibiting a close match in coefficient of thermal expansion with that of said superalloy and comprising a glass-ceramic having a composition, on an oxide basis in weight percent, selected from the group consisting of a barium silicate system and a strontium silicate system, the barium silicate system being essentially free from R$_2$O and B$_2$O$_3$ and containing 20–65% BaO and 25–65% SiO$_2$, the strontium silicate system being essentially free from B$_2$O and B$_2$O$_3$ and containing 20–60% SrO and 30–70% SiO$_2$, each system additionally consisting essentially of at least one oxide selected from the group consisting of up to 15% Al$_2$O$_3$, up to 15% ZrO$_2$, up to 15% Y$_2$O$_3$, up to 25% MnO, up to 25% NiO, up to 30% MgO, up to 30% CoO, and up to 40% iron oxide, the total of all such additions not exceeding 50% in the barium silicate system and not exceeding 40% in the strontium silicate system, wherein the glass-ceramic in the barium silicate system contains a primary crystal phase selected from the group consisting of a barium silicate-type and cristobalite and the glass-ceramic in the strontium silicate system contains a primary crystal phase selected from the group consisting of a strontium silicate-type and cristobalite, in each system there being cristobalite crystals concentrated adjacent to the interface between the glass-ceramic and the superalloy.

2. An article in accordance with claim 1 wherein the selected oxide i up to 15% $Al_2O_3$.

3. An article in accordance with claim 1 wherein the selected oxide i up to 15% $ZrO_2$.

4. An article in accordance with claim 1 wherein the selected oxide i up to 15% $Y_2O_3$.

5. An article in accordance with claim 1 wherein the selected oxide i up to 25% MnO.

6. An article in accordance with claim 1 wherein the selected oxide i up to 30% CoO.

7. An article in accordance with claim 1 wherein the selected oxide is up to 40% iron oxide.

8. An article in accordance with claim 1 wherein the selected oxide is MgO.

9. An article in accordance with claim 1 wherein the glass-ceramic composition additionally contains at least one oxide selected from the group composed of 0-25% ZnO, 0-20% CaO, 0-10% $TiO_2$, and 0-20% $Nb_2O_5$, the total content of said oxides being not over 25%.

10. An article in accordance with claim 1 wherein the glass-ceramic composition additionally contains up to 20% CaO.

11. An article in accordance with claim 1 wherein the glass-ceramic composition additionally contains up to 25% ZnO.

12. An article in accordance with claim 1 wherein the glass-ceramic composition is from the strontium silicate system and additionally contains up to 20% BaO.

13. An article in accordance with claim 1 wherein the glass-ceramic composition from the barium silicate system additionally contains up to 20% SrO.

14. An article in accordance with claim 1 wherein the glass-ceramic composition additionally contains up to 10% $TiO_2$.

15. An article in accordance with claim 1 wherein the glass-ceramic composition additionally contains up to 20% $Nb_2O_5$.

16. An article in accordance with claim 1 wherein the glass-ceramic composition additionally contains up to 10% F in excess of the oxides.

17. An article in accordance with claim 1 wherein the glass-ceramic composition consists essentially of BaO, $SiO_2$ and 1-10% by weight $Al_2O_3$, the $SiO_2$ and BaO being present in a mole ratio of between about 2:1 and 5:1.

18. An article in accordance with claim 1 wherein the glass-ceramic composition consists essentially of SrO and $SiO_2$, the mole ratio of $SrO:SiO_2$ being between 1:1.5 and 1:4, and 5 to 10 mole percent of $Al_2O_3$ or $ZrO_2$.

19. An article in accordance with claim 1 wherein the primary crystal phase is a barium silicate and the glass-ceramic composition contains up to 15% of at least one oxide selected from up to 15% $Al_2O_3$, up to 15% $ZrO_2$ and up to 15% $Y_2O_3$.

20. An article in accordance with claim 1 wherein the glass-ceramic is essentially free of an aluminosilicate crystal phase.

21. An article in accordance with claim 1 wherein the glass-ceramic composition is from the strontium silicate system.

22. An article in accordance with claim 1 wherein the glass-ceramic composition is from the barium silicate system.

* * * * *